United States Patent [19]

Scheicher

[11] 4,191,747

[45] Mar. 4, 1980

[54] CORRECTIVE AGENT FOR THE COVERING AND/OR FILLING OF BONE DEFECTS, METHOD FOR THE PREPARATION OF SAME AND METHOD OF USING THE SAME

[76] Inventor: Hans Scheicher, Rondell Neuwittelsbach 4, D-8000 Munich, Fed. Rep. of Germany

[21] Appl. No.: 860,651

[22] Filed: Dec. 14, 1977

[30] Foreign Application Priority Data

Dec. 17, 1976 [DE] Fed. Rep. of Germany ....... 2657370

[51] Int. Cl.$^2$ .................... A61K 37/48; A61K 35/32; A61K 37/00; A61K 31/70
[52] U.S. Cl. ....................................... 424/94; 424/95; 424/177; 424/180; 424/227; 424/228; 424/229; 424/271; 106/35
[58] Field of Search .................... 424/180, 177, 95, 94; 106/35

[56] References Cited

U.S. PATENT DOCUMENTS

| | | | |
|---|---|---|---|
| 2,642,375 | 6/1953 | Henderson et al. ................. | 424/180 |
| 3,476,855 | 11/1969 | Balassa .................................. | 424/95 |
| 3,703,575 | 11/1972 | Thiele .................................. | 424/95 |

FOREIGN PATENT DOCUMENTS 2502884 7/1976 Fed. Rep. of Germany .
2625289 9/1976 Fed. Rep. of Germany .

OTHER PUBLICATIONS

Soumireu'4 Mourat–Chem. Abst., vol. 75 (1971) p. 25423b.
Thomson–Chem. Abst., vol. 32 (1938) p. 9284$^8$.
Loeper–Chem. Abst., vol. 11 (1917) p. 967$^2$.

*Primary Examiner*—Sam Rosen
*Attorney, Agent, or Firm*—Sughrue, Rothwell, Mion, Zinn and Macpeak

[57] ABSTRACT

A corrective agent used for the covering and/or filling of bone defects, comprising a solution forming a gel at body temperature which comprises a physiological saline solution containing at least one polysaccharide and/or gelatin. Other additives may also be present.

The corrective agent can be prepared by boiling the at least one polysaccharide and/or gelatin in the physiological saline solution to dissolve and sterilize. The corrective agent is then generally maintained above the temperature at which solidification to a gel occurs until use, though it may be gelled and once reheated. Other additives may also be present, with time of addition depending upon the thermal susceptibility of the additives.

The corrective agent is used by coating the same on the area to be covered and/or filled.

36 Claims, No Drawings

CORRECTIVE AGENT FOR THE COVERING AND/OR FILLING OF BONE DEFECTS, METHOD FOR THE PREPARATION OF SAME AND METHOD OF USING THE SAME

BACKGROUND OF THE INVENTION

1. Field of the Invention

The invention relates to a corrective agent for the covering and/or filling of bone defects, especially for the insertion of enossal implants, to a method for preparing the same and to a method of using the same.

2. Description of the Prior Art

There is always a considerable danger of infection at the site of a bone defect, typically as formed in the case of a break, operation and/or implant in the bone tissue. The danger is particularly acute in the case of enossal half-implants—i.e., in cases where the bone tissue and a foreign body implanted into the bone tissue are no longer completely embedded in the tissue and a part of the foreign body projects above the surface of the soft tissue. This is due to the fact that in this case bacteria can penetrate between tissue and the foreign body during the healing process, and instead of the implant and the bone growing together, inflammation of the surrounding tissue often results, which in turn leads to the implant being pushed out or at least to invagination of soft tissue between the implant and the bone. The prospects of such operations being successful are thus considerably reduced.

Considerable difficulties are thus encountered with techniques as discussed above, especially in the case of inserting dental half-implants, a procedure being used to an increasing extent nowadays. The gap between the bone tissue and the implant is kept as small as possible so as to guarantee a rapid ingrowth of the implant and to restore the tooth's function as soon as possible. This gap is normally filled by blood clots which are subsequently transformed into bone tissue by the ingrowth of osteoblasts. If the blood clotting is impaired or there is infection of the blood clots, inflammation of the surrounding bone tissue often ensues, with the result that the implant is pushed out. Similar problems are encountered with the cement-free insertion of hip joints, as is currently being practised on younger patients, and with the operative treatment of chronic osteomyelitis.

SUMMARY OF THE INVENTION

The present invention has as its object creating a corrective agent for the covering and/or filling of bone defects, especially for the insertion of enossal implants, that enables a sterile sealing of the wound surfaces as well as the filling of any spaces between bone tissue and implants, which corrective agent is dissolved or reabsorbed during the after- or ingrowth of the bone.

This object is reached according to the present invention by means of a solution of physiological saline solution and at least one polysaccharide and/or gelatin, which forma a gel at body temperature.

DESCRIPTION OF PREFERRED EMBODIMENTS

The term physiological saline solution referred to herein is to be understood in a broad sense—i.e., it should include every isotonic solution being tolerated by the body. Examples in this respect are the physiological saline solutions in narrower sense (solutio natrii chlorati physiologica), the so-called Ringer's solution (1000 ml contain 8.6 g sodium chloride, 0.3 g potassium chloride and 0.33 g calcium chloride), as well as blood substitute substances, i.e. infusion and standard injection solutions as are listed for example in the catalogue of pharmaceutical specialities put out by the members of the Bundesverbandes der pharmazentrischen Industrie e.V. (Federal Association of the pharmaceutical industry), with the title "Rote Liste" 1975 under the numbers 56001 to 56082; 56086 to 56267. Mixtures of these substances are also to be understood. The corrective agent according to the invention is applied to the wound surfaces at a temperature which is above the temperature at which the solution solidifies to a gel, but which, however, is below the temperature at which the tissue is permanently damaged or coagulates, this occurring typically between 50° and 53° C. In the case of the insertion of enossal dental half-implants, which can be done, e.g., using a tampon or gauze plug which has been soaked in the corrective agent itself, the bleeding is stopped and then the wall of the bone cavity is either covered with the corrective agent or else the whole bone cavity is filled with it. The implant is subsequently inserted so that the entire region between the wall of the bone cavity and the implant is filled by the corrective agent. Since the corrective agent immediately solidifies to a gel on cooling to body temperature, it is not immediately washed out by the wound secretions and thus serves as a sterile sealing agent in the wound cavity during the initial stages of the healing process. The choice of materials ensures, however, that the corrective agent is either dissolved or reabsorbed with increasing ingrowth of the bone tissue and does not remain as an intermediate layer between the bone tissue and the implant to be held.

The corrective agent according to the invention can also be used in cases of open bone fractures, nailings and other bone operations, in which case it is applied to the bone as a covering layer and fills any cavities formed, as well as in cases of operative therapy for chronic osteomyelitis, where it is used in place of the so-called Eigenblut-Antibiotica-Plombe (autohemo-antibiotic filling) (see Münchener Medizinische Wochenschrift 112. No. 36, pgs. 1585-90/1970, article by H. Ecke; also Therapiewoche 23, No 21, 1868, 1870, 1873/1973, article by A. Bikfalvi).

A process whereby the pores of a porous outer layer of an implant are closed before use by means of applying and drying a layer of a water-soluble substance, e.g., gelatin or a similar material, which is subsequently sterilized, rendered anti-bacterial and is dissolved by the body juices after implantation, thus allowing the tissue cells to grow into the now freed pores, is disclosed in DT-OS No. 2 154 272.

According to a particularly preferred embodiment of the present invention, the corrective agent according to the invention contains a substance stimulating tissue diffusion, in particular a hyaluronidase, in a quantity of about 7 I.U. to about 800 I.U., preferably about 60 I.U. to about 90 I.U., per cm$^3$ of liquid corrective agent. The substance stimulating tissue diffusion, when contained in the gel, will diffuse into the adjacent tissue and aid in the disintegration of blood clots there and assist the circulation necessary for growth, as well as in the removal of waste products.

With respect to the hyaluronidase, attention is drawn to the book "*The Enzymes*" pgs. 307 ff., editor Paul D. Boyer, vol. V 3, edition Academ Press 1971, and to the Chemielexicon Römpp, 1974 p. 1523. As an example of a suitable hyaluronidase the preparation kinetin, from Schering A.G., D 1000 Berlin 65, could be mentioned.

The corrective agent preferably contains further an addition of an antibiotic and/or a sulfonamide. When using antibiotics and/or sulfonamides which are usually administered parenterally or intravenously, the addition is expediently calculated in a quantity of about 0.01–about 10% of the effective substance in the normal daily dose per individuum to 1 cm$^3$ of the liquid corrective agent. A favourable range for the addition is between 0.1 and 3%, preferably about 0.4–1%. When using antibiotics and sulfonamides intended for local application, such as e.g. terramycin powder (produced by Pfitzer, Germany), it is advantageous to add 0.05–0.5 g, preferably about 0.1 g of the powder per 1 cm$^3$ of the liquid corrective agent.

When using powdered marbaletten (produced by Boyer, Germany), about 1–10, preferably 1–3 tablets are added per 1 cm$^3$ of liquid corrective agent.

The designation antibiotics is to be generally understood here. Thus under antibiotics penicillins, cephalosporins, chloramphenicols, lincomycins and macrolides, peptolides and polypeptides are to be understood, as well as steptomycines and tetracyclines. Examples of such antibiotics are listed in the catalogue of pharmaceutical specialities put out by the members of the Bundesverbandes der pharmazentrischen Industrie e.V. with the title "Rote Liste", 1975, under the numbers 11001 to 11220. Examples of the sulfonamides are listed in the above-mentioned "Rote Liste" under the numbers 86001 to 86045. If the corrective agent contains antibiotics and/or sulfonamides, a test for any corresponding allergies is to be made before its application.

Inclusion of an antibiotic and/or sulfonamide in the gel results in a depot effect of the antibiotic and/or sulfonamide, these normally being washed out of the wound cavity immediately by the formation of wound secretions. In connection with the material stimulating tissue diffusion, the movement of the antibiotic or sulfonamide into the surrounding tissues is facilitated, and the depth effect of the antibiotic or sulfonamide is also improved.

It is particularly expedient if the corrective agent contains as additives substances stimulating bone formation and/or bone growth which diffuse slowly out of the gel into the forming bone without being prematurely rinsed out.

Substances particularly suitable for stimulating bone formation and/or bone growth include sodium, lithium, carbon, magnesium, boron, fluorine, silicon, phosphorus, calcium, potassium and/or yttrium ions, and/or ions of the rare earths, these substances being added to the corrective agent in body-soluble form. Sodium, calcium, boron and phosphorus ions are particularly favourable. The suitability of these previously-known ions for stimulating the growth of bone tissue onto vitrified aluminum oxide ceramic is known from DT-AS 23 24 867. There, however, these ions are diffused into the surface of the implant by thermal diffusion, an expensive and difficult technical process. A further difficulty arising in this prior art process is the dosage of the ions and the period of time during which they are delivered to the tissue. In the case of the corrective agent according to the invention, the dosage of ions can be more simply regulated by means of adding them to the corrective agent solution.

For an ingrowth of implants powdered apatite crystals, e.g., ground in a mortar, which are known to strongly accelerate bone regeneration, are preferably introduced into the gel. Besides natural bone apatites, apatites being isomorphic to hydroxylapatite seem especially suitable, in particular very small calcium phosphate hydroxylapatite crystals. The addition involves about 0.2–70 wt.%, preferably about 10–20 wt.% relative to the quantity of liquefied agent, not yet being provided with additives and being able to gel.

Further substances stimulating bone growth are described in the DT-OS No. 2606540. When ground to a powder they can serve as the additive mentioned.

Through their resorption, ions which stimulate the growth of new bone tissue form at the interfaces. This advantage could not be exploited with previous techniques since the apatites were quickly rinsed out and their dosage at the required site(s) was difficult.

Particularly in those cases where large cavities in the bone are to be filled, it is advisable to use a variant of the corrective agent according to the invention; in this case denatured bone meal is added to the liquid corrective agent. The proportion of bone meal relative to the quantity of liquid corrective agent, being not yet provided with additives and able to gel, is about 2.5 wt.% to about 60 wt.%, preferably about 5 wt.% to about 20 wt.%.

In the following, an example for the manufacture of denatured bone meal is given:

Calves' vertebrae are dried at 100° C. for 8 hours. The dried bones are coarsely ground and subsequently freed from fat by leaving in ether for 24 hours. After drying off the ether the bone meal is left 24 hours in 20% hydrogen peroxide and then boiled for 10 minutes in same. The hydrogen peroxide is then poured off and the material subsequently dried. The powder obtained in this way from macerated bones is ground very finely in a mortar and then sterilized in an autoclave (this procedure is based on work by R. and A. Baumeister—see J. Bone Surg. 39 A 153 (1957) ).

The polysaccharides used as a component of the corrective agent according to the invention must be capable of gelling, i.e. their solutions in physiological saline solution in the broader and narrower senses referred to previously must, after cooling to body temperature, have solidifed to a firm gel. Preferable polysaccharides of this sort are agar, further processed products of agar or agar derivatives, since their solidification temperature lies in the region of 42° C. Pectin and carrageen belong further to the gel-forming polysaccharides, also carubin and duaran which do not gel themselves but do so when mixed with other gel-forming polysaccharides which favour gelling. Mixtures of different gel-forming polysaccharides are also suitable. Agarose has proved to be especially favourable, which, depending on the concentration of the solution, solidifies between approximately 35° and 45° C. (details concerning the polysaccharides mentioned can be obtained from the following literature sources: Rompp, Chemie-lexicon 1974, p. 88, and the literature referred to there; Ullmann, vol. 13 pgs. 184 ff.; Araki (C.) Bull Chem. Soc. Japan 29 1956 p. 543; US-PS 34 23 396

According to a particularly advantageous embodiment the corrective agent according to the invention for covering and/or filling bone defects contains as a gel-forming solution a 0.6 wt.% to about 30 wt.%, preferably an approximately 1 wt.% to about 3 wt.% solution of agarose in physiological saline solution (solutio natrii chlorati physiologica).

Of the various sorts of gelatine, (see U.S. Pharmacopoe USP XVII 1970) the only ones suitable are those which, inisotonic solution that is tolerated by the body, form a stable gel at body temperature; i.e. a gel solidifying under 35° C., preferably under 40° C., whose dissimilation in the body of a person or an animal is only completely finished after a period of some days or weeks. Gelatine-Schwamm could be mentioned for example, as is used for Hemostasis (produced by Behringewerke Braun-Melsungen). Mixtures of gelatin and the previously-mentioned gel-forming polysaccharides which can, in isotonic solution, form gels at body temperature, can be used for the corrective agent according to the invention. Further details about gelatin can be taken from the Achema Jahresbericht 1970 p. 1223, the Chemie Lexicon Rompp, 1974 p. 1242 ff., and the literature referred to there, as well as from the brochure by Rudolf Hinterwaldner "Struktur und Eigenschaften des Kollagens und seiner Umwandlungsprodukte", Ermittlungs- und Berichtedienst Moser-Verlag, Garmisch-Partenkirchen Archiv Nr. 899 SKB. No. F. 1940. The optimal concentrations of the gel-forming substances in the corrective agent according to the invention required in each case for the formation of a stable gel, i.e. the polysaccharides and/or gelatine in the corresponding isotonic solutions, can be determined by simple experiments. Suitable concentrations of the gel-forming substances mentioned, relative to the isotonic solution designated as physiological saline solution in a broader sense, are about 0.5-30 wt.%, preferably about 2-5 wt.%.

The present invention also relates to a method for the preparation of a corrective agent for the covering and/or filling of bone defects, in particular for the insertion of enossal implants, this aspect of the invention being characterized in that at least one polysaccharide and/or gelatin in physiological saline solution is boiled to effect dissolution and sterilization for about 5-30 minutes, preferably about 10-15 minutes, the type and quantity of the one or more polysaccharides and/or the gelatin being so calculated that on cooling to body temperature a stable gel is formed, and that the solution is maintained at a temperature above the temperature at which the gel forms, preferably at about 50° C. until it is required for use.

According to a further preferred refinement of this method, the solution obtained has added thereto approximately 2.5 wt.% to about 60 wt.%, preferably 5 wt.% to about 20 wt.%, relative to the quantity of liquid agent, of denatured bone meal and/or substances which stimulate bone formation or bone growth as earlier examplified, preferably apatite crystals in powder form and/or sodium, lithium, carbon, magnesium, boron, fluorine, silicon, phosphorus, calcium, potassium and/or yttrium ions and/or ions of the alkaline earths in body-soluble form.

In a modification of the previously-described method the one or more polysaccharides and/or the gelatin have added thereto, before their dissolution and boiling in the physiological saline solution, about 2.5 wt.% to about 60 wt.%, preferably about 5 wt.% to about 20 wt.%, relative to the quantity of physiological saline solution, of denatured bone meal and/or substances stimulating bone formation or bone growth, preferably apatite crystals in powder form and/or sodium, lithium, carbon, magnesium, boron, fluorine, silicon, phosphorus, calcium, potassium and/or yttrium ions and/or ions of the rare earths in body-soluble form.

Thus, for example, one starts with a dry substance containing at least one gel-forming polysaccharide and mixes this with the denatured bone meal and perhaps the bone-forming substances. Before use, this dry mixture is mixed with a corresponding quantity of physiological saline solution and is boiled for about 5-30 minutes, preferably about 10-15 minutes, to effect complete sterilization of the gel-forming substance. The solution, having been sterilized by boiling in an autoclave, is subsequently cooled and kept at a temperature above the solidification point thereof by means of a thermostat until required for use. When applying the solution to an open bone wound, care is taken that the solution is not warmer than about 50° C., preferably exhibiting a temperature of about 40°-45° C.

According to a variant of the method according to the invention, the sterilized solution has added to it a substance stimulating tissue diffusion, particularly hyaluronidase, in a quantity of about 7 I.U. to about 800 I.U., preferably about 60 I.U. to about 90 I.U., per $cm^3$ of solution, and/or an antibiotic and/or a sulfonamide in the previously-given quantities and at a temperature which is above that at which solidification to a gel occurs and below that at which the substances mentioned are subject to thermal damage. Temperatures below 50° C., preferably between 45° and 50° C., are suitable here.

In the method according to the invention, agar products or agar derivatives, particularly agarose, are used as polysaccharides. The agarose is expediently mixed with physiological saline solution as agarose powder in a proportion of approximately 0.6 wt.% to about 30 wt.%, preferably about 1 wt.% to about 3 wt.%, and is subsequently boiled sterile. The denatured bone meal and/or bone-forming substances may be added prior to, with or subsequent to the agarose.

For practical use of the corrective agent, it is particularly advantageous if the sterilized solution of physiological saline solution and at least one polysaccharide and/or gelatin with optimal denatured bone meal and/or substances stimulating bone formation or bone growth is prepared in disposable syringes. The syringes filled with the liquid solution are stored at a temperature above that at which the solution solidifies to a gel and are directly available for use. It is also possible to cool the sterilized solution in the syringes and thus let it solidify to a gel. In this case, the syringes containing the sterilized solution must be warmed above the hysteresis point of the gel prior to use, preferably by putting the syringes with their contents into boiling water or steam for about 2-5 minutes. The gelling and reliquefaction should, however, not be repeated more than once since in so doing the corrective agent undergoes an alteration which impairs its properties.

If the corrective agent according to the invention is to contain substances stimulating tissue diffusion and/or antibiotics, it is essential, in order to avoid thermal damage, to add these to the solution after it has been sterilized and already cooled, being however still above the solidification temperature. Denatured bone meal and/or substances stimulating bone formation or bone growth can also be added at the same time, if these have not already been added during the boiling of the one or more polysaccharides and/or the gelatin with the physiological saline solution.

The addition of various optimal additives as mentioned above can best be done by preparing samples of the agent stimulating tissue diffusion and/or the antibiotic and/or the substances stimulating bone formation or bone growth and/or the denatured bone meal in sterile form in dry ampoules, the quantities corresponding in each case to the quantity of sterilized solution taken up in a syringe. The volume of the dry ampoules must be so calculated as to enable them to take up the sterilized solution contained in a syringe. Before using the corrective agent according to the invention, the sterilized solution is injected from the respective disposable syringe into the opened ampoule at a temperature above that at which solidification to a gel occurs but below 50° C., which temperature is harmful to the agents added, is mixed with the substances contained therein and subsequently is drawn up again into the disposable syringe, if necessary after a further thermostatic storage during which the temperature may not drop below that at which solidification to a gel occurs, whereafter the corrective agent is finally applied.

According to a further variant of the method which is particularly advantageous for the distribution and practical use of the corrective agent, one fills the physiological saline solution and the one or more polysaccharides and/or gelatin with optimal denatured bone meal and/or substances stimulating bone formation or bone growth and perhaps the sulfonamide, in sterile form, into ampoules before boiling.

The ampoules can be stored until the corrective agent is required, whereupon their contents are boiled to effect dissolution and sterilization, preferably by introducing the ampoules into a boiling water bath or steam. The resulting solution, which forms a gel on cooling, is drawn up into a disposable syringe before the temperature drops to that at which solidification to a gel occurs, the syringe already containing a sample, corresponding to the quantity contained in each ampoule, of the agent stimulating tissue diffusion and/or the antibiotic and/or the substance stimulating bone formation or bone growth and/or the denatured bone meal and even the sulfonamide.

If the sterilized, gel-forming solution in the ampoule is not immediately required, after cooling and solidification it can be heated once more and made ready for use. This process, however, for reasons already mentioned, cannot be repeated an arbitrary number of times. However, once the sterilized, gel-forming solution has been mixed with the agent stimulating tissue diffusion and/or with the antibiotic, reprocessing after solidification to a gel is impossible since the agent stimulating tissue diffusion and the antibiotic are destroyed by heating to the liquefaction temperature of the gel and lose their effectivity.

The agent according to the invention, prepared by one of the previously-described methods or by a similar method, is preferably used for the insertion of enossal implants, in particular dental half-implants. The agent can be used to fill the alveoli resulting after extraction of a tooth. After cooling of the liquid solution to body temperature a "gel plug" is formed which prevents the penetration of bacteria and seals the wound. In this way the formation of a "dry alveolus" is prevented. The probability of after-bleeding and swelling is also reduced. Substances promoting bone growth and/or the denatured bone meal lead to rapid callus formation and to only a small atrophying of the bone. Substances stimulating tissue diffusion and/or an antibiotic or a sulfonamide accelerate the healing process in the bone and surrounding soft-part tissues, eg. gum tissues.

If an enossal dental half-implant is to be inserted into the alveolus of the extracted tooth, if necessary after deepening of the alveolus, a gauze plug or tampon which has been saturated with the corrective agent according to the invention is put into the alveolus immediately after extraction, if necessary after stopping the bleeding. This procedure can also be used when no implant is to be inserted into the alveolus of the extracted tooth, since it favours the healing process in this case too. After the period necessary for the preparation of the actual implantation process, the gel-soaked gauze plug or tampon is removed and, after repeated smoothing over of the wound surface with the corrective agent according to the invention, the implant is inserted. Due to the homogeneous sealing of the wound surface, approximately fourteen days can elapse between extraction and implantation.

The following non-limiting examples are offered to further illustrate the present invention. In each Example the sterilized solution is always withdrawn with a 2 $cm^3$ glass syringe. The sterilized additives are measured quantitatively into 2 $cm^3$ dry ampoules.

EXAMPLE 1

2 g of agarose powder are boiled with 100 ml of physiological saline solution for half an hour. After natural cooling to 50° C., 2 $cm^3$ of the resulting sterilized solution are mixed with 150 I.U. hyaluronidase (product "Kinetin" of the firm Schering) and about 10 mg terramycine powder and kept under thermostatic control at a temperature of 50° C. until required. The material was used for the insertion of enossal dental half-implants.

In so doing the alveolus of the extracted tooth was first dried with a tampon or gauze swab which had been soaked in the liquid corrective agent. The alveolus was subsequently filled with a similarly soaked gauze plug, which was only removed just before inserting the implant i.e. after 48 hours. The alveolus was then brushed and almost filled with the liquid corrective agent before the implant was pushed in and made firm.

EXAMPLE 2

2 $cm^3$ of the solution prepared as according to Example 1 are additionally mixed with about 20 mg powdered apatite crystals. A mixture is obtained being particularly suitable for the insertion of implants.

EXAMPLE 3

2 $cm^3$ of the solution according to Example 1 are mixed with 0.7 g denatured bone meal, which is prepared according to the previously-described method by R. and A. Baumeister. The solution obtained is particularly useful for the filling of cavities created in the case of bone operations. The sterilized solution is taken up in each case with a 2 $cm^3$ glass syringe. The additives, in sterile form, are stored to correspond in 2 $cm^3$ dry ampoules.

While the invention has been described in detail and with reference to specific embodiments thereof, it will be apparant to one skilled in the art that various changes and modifications can be made therein without departing from the spirit and scope thereof.

What is claimed is:

1. A corrective agent for the covering and/or filling of bone defects, comprising a physiological saline solution containing (1) at least one polysaccharide and/or gelatin and (2) at least one substance stimulating bone formation and/or bone growth, said solution being in liquid solution form at a temperature above body temperature but below the temperature at which body tissue is permanently damaged or coagulates and said solution forming a stable gel at body temperature.

2. A corrective agent according to claim 1, further containing a substance stimulating tissue diffusion in a quantity of about 7 I.U. to about 800 I.U. per cm³ of liquid in the corrective agent.

3. A corrective agent according to claim 2 wherein said substance stimulating tissue diffusion is hyaluronidase.

4. A corrective agent according to claim 2 wherein the quantity of said substance stimulating tissue diffusion is about 60 I.U. to about 90 I.U. per cm³ of liquid in the corrective agent.

5. A corrective agent according to claim 1, containing an antibiotic and/or a sulfonamide.

6. A corrective agent according to claim 1, wherein at least one substance stimulating bone formation and/or bone growth comprises apatite crystals in powder form.

7. A corrective agent according to claim 1, wherein at least one substance stimulating bone formation and/or bone growth comprises sodium, lithium, carbon, magnesium, boron, fluorine, silicon, phosphorus, calcium, potassium and/or yttrium ions and/or ions of the rare earths in body-soluble form.

8. A corrective agent according to claim 1, further comprising about 2.5 wt. % to about 60 wt. % of denatured bone meal, based on the quantity of physiological saline solution used.

9. A corrective agent according to claim 8, comprising from about 5 wt. % to about 20 wt. % of said denatured bone meal.

10. A corrective agent according to claim 1, wherein said polysaccharide is an agar product.

11. A corrective agent according to claim 1, wherein said polysaccharide is an agar derivative.

12. A corrective agent according to claim 1, wherein said polysaccharide is agarose.

13. A corrective agent according to claim 12, wherein approximately 0.6 wt.% to about 30 wt.% of agarose is present in said physiological saline solution.

14. A corrective agent according to claim 12, wherein approximately 2 wt.% to about 2.5 wt.% of agarose is present in said physiological saline solution.

15. A corrective agent according to claim 1 wherein agarose is used without the presence of gelatin.

16. A corrective agent according to claim 1 wherein at least one polysaccharide is used without the presence of gelatin.

17. A method of covering and/or filling bone defects which comprises applying to the defective area in flowable liquid form as a corrective agent a physiological saline solution containing at least one polysaccharide and/or gelatin at a temperature above body temperature but below the temperature at which body tissue is permanently damaged or coagulates and then allowing said solution to cool to a stable gel, whereby cavities formed around the defect are filled and where an implant is used, any gaps between the defect and the implant are filled.

18. A method according to claim 17, wherein said solution is maintained is at about 50° C.

19. A method according to claim 17, wherein about 2.5 wt.% to about 60 wt.% of denatured bone meal, based on the quantity of physiological saline solution in the corrective agent, and/or at least one substance stimulating bone formation or bone growth, are added to the solution in body-soluble form.

20. A method according to claim 19, wherein about 5 wt.% to about 20 wt.% of said denatured bone meal and/or said substances stimulating bone formation or bone growth are added to said solution.

21. A method according to claim 20, wherein at least one substance stimulating bone formation or bone growth is apatite crystals in powder form and/or sodium, lithium, carbon, magnesium, boron, fluorine, silicon, phosphorus, calcium, potassium and/or yttrium ions and/or ions of the rare earths.

22. A method according to claim 17, wherein about 2.5 wt.% to about 60 wt.% of denatured bone meal, based on to the quantity of physiological saline solution in the corrective agent, and/or at least one substance stimulating bone formation or bone growth, are added in body-soluble form to the one or more polysaccharides and/or gelatin before their dissolution in physiological saline solution.

23. A method according to claim 22, wherein about 5 wt.% to about 20 wt.% of said denatured bone meal and/or said substances stimulating bone formation or bone growth are added to said solution.

24. A method according to claim 22, wherein at least one substance stimulating bone formation or bone growth is apatite crystals in powder form and/or sodium, lithium, carbon, magnesium, boron, fluorine, silicon, phosphorus, calcium, potassium and/or yttrium ions and/or ions of the rare earths.

25. A method according to claim 17, wherein a substance stimulating tissue diffusion in a quantity of about 7 I.U. to about 800 I.U. per cm³ of solution, and/or about 0.05 mg to about 500 mg of an antibiotic and/or sulfonamide per cm³ of solution are added to the solution.

26. A method according to claim 25, wherein said substance stimulating tissue diffusion is hyaluronidase.

27. A method according to claim 25, wherein the quantity of said substance stimulating tissue diffusion is about 60 I.U. to about 90 I.U. per cm³ of corrective agent.

28. A method according to claim 17, wherein said polysaccharide is an agar product.

29. A method according to claim 17, wherein said polysaccharide is an agar derivative.

30. A method according to claim 17, wherein said polysaccharide is agarose.

31. A method according to claim 30, wherein about 0.6 wt.% to about 30 wt.% of said agarose in powder form is mixed and boiled with the physiological saline solution.

32. A method according to claim 30, wherein 2 wt.% to about 3 wt.%, of said agarose in powder form is mixed and boiled with the physiological saline solution.

33. A method according to claim 17, wherein the solution in sterilized form is filled into a disposable syringe, and a sample corresponding to a quantity to be taken up in the disposable syringe, of at least one of an agent stimulating tissue diffusion, an antibiotic, a sulfonamide, a substance stimulating bone formation or bone growth, and denatured bone meal is prepared in sterile form in a dry ampoule, the sterilized solution is injected at a temperature above that at which solidification thereof to a gel occurs from the disposable syringe into the ampoule, is mixed with the material contained therein, and is subsequently drawn up again into the disposable syringe.

34. A method according to claim 17, wherein the physiological saline solution and at least one of the polysaccharide and/or gelatin is filled into an ampoule, stored therein, and boiled therein to effect solution and sterilization before use.

35. A method according to claim 34, wherein a sample corresponding to a quantity to be taken up in said ampoule, of at least one of an agent stimulating tissue diffusion, an antibiotic, a sulfonamide, a substance stimulating bone formation or bone growth and denatured bone meal is filled into a disposable syringe, into which the said boiled physiological saline solution is drawn up into from the ampoule at a temperature above that at which solidification to a gel occurs.

36. A method according to claim 32, wherein 2.5 weight % of said agarose in powder form is mixed and boiled with the physiological saline solution.

* * * * *